(12) United States Patent
Schmalenberg et al.

(10) Patent No.: US 11,878,663 B2
(45) Date of Patent: Jan. 23, 2024

(54) AUTONOMOUS VEHICLE CLEANING SYSTEM USING FOLDABLE SEATS AND ADJUSTABLE LIGHTING CONDITIONS

(71) Applicant: TOYOTA MOTOR ENGINEERING & MANUFACTURING NORTH AMERICA, INC., Plano, TX (US)

(72) Inventors: Paul D. Schmalenberg, Pittsburgh, PA (US); Sean P. Rodrigues, Ann Arbor, MI (US); Atsushi Iwai, Pittsburgh, PA (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 523 days.

(21) Appl. No.: 17/172,247

(22) Filed: Feb. 10, 2021

(65) Prior Publication Data

US 2022/0250588 A1 Aug. 11, 2022

(51) Int. Cl.
*B60S 1/64* (2006.01)
*A61L 2/10* (2006.01)

(52) U.S. Cl.
CPC . *B60S 1/64* (2013.01); *A61L 2/10* (2013.01); *A61L 2202/11* (2013.01); *A61L 2202/14* (2013.01); *A61L 2202/17* (2013.01)

(58) Field of Classification Search
CPC .......... B60S 1/64; A61L 2/10; A61L 2202/11; A61L 2202/14; A61L 2202/17; A61L 2202/16; A61L 2202/25; B60N 2/002; B60N 2/0244; B60Q 2800/10; B60Q 3/68; B60Q 3/70; B60Q 3/80
See application file for complete search history.

(56) References Cited

U.S. PATENT DOCUMENTS

| | | | |
|---|---|---|---|
| 10,304,165 B2 | 5/2019 | Tokatyan | |
| 10,632,975 B2 * | 4/2020 | Strasdat | B08B 1/006 |
| 11,334,985 B2 * | 5/2022 | Ventimiglia | G06Q 10/00 |
| 11,730,844 B1 * | 8/2023 | Hong | A61L 2/10 |
| | | | 422/2 |
| 2017/0210352 A1 | 7/2017 | Stauffer et al. | |
| 2019/0263231 A1 * | 8/2019 | Jabour | B60R 16/037 |
| 2020/0186689 A1 | 6/2020 | Outwater et al. | |
| 2021/0034888 A1 * | 2/2021 | Ye | G06V 20/59 |
| 2022/0125975 A1 * | 4/2022 | MacKenzie | B60Q 9/00 |

FOREIGN PATENT DOCUMENTS

WO 2020170680 A1 8/2020

* cited by examiner

*Primary Examiner* — Michael J Zanelli
(74) *Attorney, Agent, or Firm* — HAYNES AND BOONE, LLP

(57) ABSTRACT

A vehicle includes an interior and an exterior, a surface within the interior, and a movable seat positioned over a first portion of the surface. The vehicle also includes a processor, a seat control system able to move the seat to expose the portion of the surface, and a light source able to illuminate a larger second portion of the surface which includes the first portion. The vehicle further includes a sensor to capture an image of the second portion of the surface, illuminated by the light source, and a cleaning element able to clean the second portion of the surface. The processor is configured to detect foreign material on the second portion of the surface, based on a comparison between the image and a stored image. The processor is also configured to activate the cleaning element, after detecting the foreign material on the second portion of the surface.

20 Claims, 5 Drawing Sheets

AUTONOMOUS VEHICLE CLEANING SYSTEM USING FOLDABLE SEATS AND ADJUSTABLE LIGHTING CONDITIONS

TECHNICAL FIELD

The subject matter described herein relates to an autonomous cleaning system for vehicle interiors. This autonomous vehicle cleaning system has particular, but not exclusive, utility for maintaining cleanliness of Mobility-as-a-Service (MaaS) cars, vans, and trucks.

BACKGROUND

Ultraviolet (UV) light emission is a known technology used to clean the inside surfaces of a vehicle by killing bacteria/viruses, breaking down organic molecules, and bleaching. Although UV lights are used to clean surfaces within the vehicle, UV lights do not always reach hard-to-reach spaces or clean deep stains. Passengers may enter a vehicle and notice that there are some areas of a vehicle that aren't actually clean even though UV lights had been activated prior to their entering. In some cases, a dirty vehicle may present health hazards, as with influenza, COVID, and other potentially deadly pathogens. UV light can also be hazardous to human health. Care must be taken to ensure humans and animals are not in the vehicle when UV cleaning lights are activated.

In Mobility-as-a-Service (MaaS) vehicles such as taxis, autonomous taxis, e-palettes, etc. it can be difficult to clean the vehicle between rides, with passengers coming and going. For autonomous MaaS vehicles to get completely clean without the help of an available driver, they need to be sent to a cleaning service facility, which must then inspect and clean the vehicle.

It should be understood that current vehicle cleaning systems and methods have numerous drawbacks, including but not limited to frequent service visits, passenger health hazards, and insufficient cleaning in hard-to-reach areas. Accordingly, a need exists for improved vehicle cleaning systems and methods that address the foregoing and other concerns.

The information included in this Background section of the specification, including any references cited herein and any description or discussion thereof, is included for technical reference purposes only and is not to be regarded as subject matter by which the scope of the disclosure is to be bound.

SUMMARY

Disclosed is an autonomous vehicle cleaning system that detects and addresses foreign material in a vehicle interior. This autonomous vehicle cleaning system may employ light sources, 2D or 3D sensors, window dimming, autonomous driving, UV sterilization, or cleaning fluids. The autonomous vehicle cleaning system may for example be activated autonomously when all occupants have left the vehicle, and may detect the locations of stains, spills, dirt, trash, debris, and other foreign material, and may either attempt to clean the surfaces on which they occur, or may autonomously deliver the vehicle to a service location for cleaning.

The autonomous vehicle cleaning system disclosed herein has particular, but not exclusive, utility cleaning MaaS vehicles in between passengers. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a vehicle with an interior and an exterior. The vehicle includes a surface disposed within the interior; a movable seat positioned over a first portion of the surface; a processor; a seat control system configured to, under control of the processor, move the movable seat such that the first portion of the surface is exposed; a light source configured to, when activated by the processor after the seat control system has moved the movable seat, illuminate a second portion of the surface, where the second portion includes the first portion; a sensor configured to, under control of the processor, capture an image of the second portion of the surface while the second portion of the surface is illuminated by the light source; and a cleaning element configured to, when activated by the processor, clean the second portion of the surface, where the processor is configured to detect foreign material on the second portion of the surface based on a comparison between the image and a stored image, where the processor is configured to, after detecting the foreign material on the second portion of the surface, activate the cleaning element. Other embodiments of this aspect include corresponding computer systems, apparatus, and computer programs recorded on one or more computer storage devices, each configured to perform the actions of the methods.

Implementations may include one or more of the following features. In some embodiments, the light source and the sensor include a lidar. In some embodiments, the light source includes an ultraviolet (UV) light source, and the sensor includes a UV, visible light, or infrared (IR) sensor. In some embodiments, the light source includes a visible light source, and the sensor includes a visible light camera. In some embodiments, the light source includes an infrared light source, and the sensor includes an infrared sensor. In some embodiments, the cleaning element is a UV lamp or a cleaning fluid delivery system. In some embodiments, the processor is configured to activate the light source while the windows are dimmed In some embodiments, the dimming or brightening includes automatic curtains, shades, louvres, visors, or electrochromic elements. In some embodiments, the processor is configured to, after detecting the foreign material on the surface, issue an alert through a display or communication module. In some embodiments, the vehicle further including an autonomous driving system configured to, under control of the processor, drive the vehicle to a destination. In some embodiments, the destination includes dim lighting, and where the processor is configured to activate the light source while the vehicle is in the destination. In some embodiments, the destination is a service location, and the processor is configured to, after detecting the foreign material, control the autonomous driving system to drive the vehicle to the destination. Implementations of the described techniques may include hardware, a method or process, or computer software on a computer-accessible medium.

One general aspect includes a method for cleaning an interior surface of a vehicle. The method includes providing a movable seat positioned over a first portion of the interior surface; under control of a processor, moving the movable seat to expose the first portion; under control of the processor after the movable seat has been moved, activating a light source to illuminate a second portion of the interior surface, where the second portion includes the first portion; with a sensor under control of the processor, capturing an image of the second portion while the second portion is illuminated by the light source; with the processor, based on a comparison between the image and a stored image, detecting foreign material on the second portion; and with the processor, after detecting the foreign material, activating a cleaning element to clean the second portion. Other embodiments of this aspect include corresponding computer systems, apparatus, and computer programs recorded on one or more computer storage devices, each configured to perform the actions of the methods.

Implementations may include one or more of the following features. In some embodiments, the light source is a laser, UV light source, visible light source, or infrared light source, and the sensor is configured to detect light produced by the light source; or the cleaning element is a UV lamp or cleaning fluid delivery system. In some embodiments, the method further includes dimming the vehicle interior before activating the light source. Implementations of the described techniques may include hardware, a method or process, or computer software on a computer-accessible medium.

One general aspect includes a system for cleaning a surface in an interior of a vehicle. The system includes the vehicle, where the vehicle includes an interior and an exterior. The system also includes a surface disposed within the interior; a movable seat positioned over a first portion of the surface; a processor; a light sensor configured to detect a lighting condition of the interior; an external light control system configured to, under control of the processor and based on the detected lighting condition of the interior, adjust an amount of external light entering the vehicle to a desired amount; an autonomous cleaning system disposed within the interior and configured to be activated by the processor after the amount of external light entering the vehicle has been adjusted to the desired amount. Other embodiments of this aspect include corresponding computer systems, apparatus, and computer programs recorded on one or more computer storage devices, each configured to perform the actions of the methods.

Implementations may include one or more of the following features. In some embodiments, adjusting the amount of external light entering the vehicle includes: adjustably dimming one or more windows of the vehicle, and where the vehicle includes automatic curtains, shades, louvres, visors, or electrochromic elements configured to adjustably dim the one or more windows; driving the vehicle to a location with a desired amount of external light. In some embodiments, the external light control system includes an autonomous driving system configured to drive the vehicle to the location; or at least partially opening or closing a garage door, and the external light control system includes an automatic garage door controller. In some embodiments, the light source is configured to, when activated by the processor after the seat control system has moved the movable seat, illuminate a second portion of the surface, where the second portion includes the first portion; and a sensor is configured to: detect light produced by the light source; and under control of the processor, capture an image of the second portion of the surface while the second portion of the surface is illuminated by the light source, where the processor is configured to detect foreign material on the second portion of the surface based on a comparison between the image and a stored image. In some embodiments, the autonomous cleaning system includes: a cleaning element configured to, when activated by the processor, clean the second portion of the surface, where the cleaning element is a UV lamp or a cleaning fluid delivery system, and where the processor is configured to, after detecting the foreign material on the second portion of the surface, activate the cleaning element. In some embodiments, the system further includes an alert, issuable via a display or communication module under control of the processor, indicating that the foreign material has been detected on the second portion of the surface. Implementations of the described techniques may include hardware, a method or process, or computer software on a computer-accessible medium.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the autonomous vehicle cleaning system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
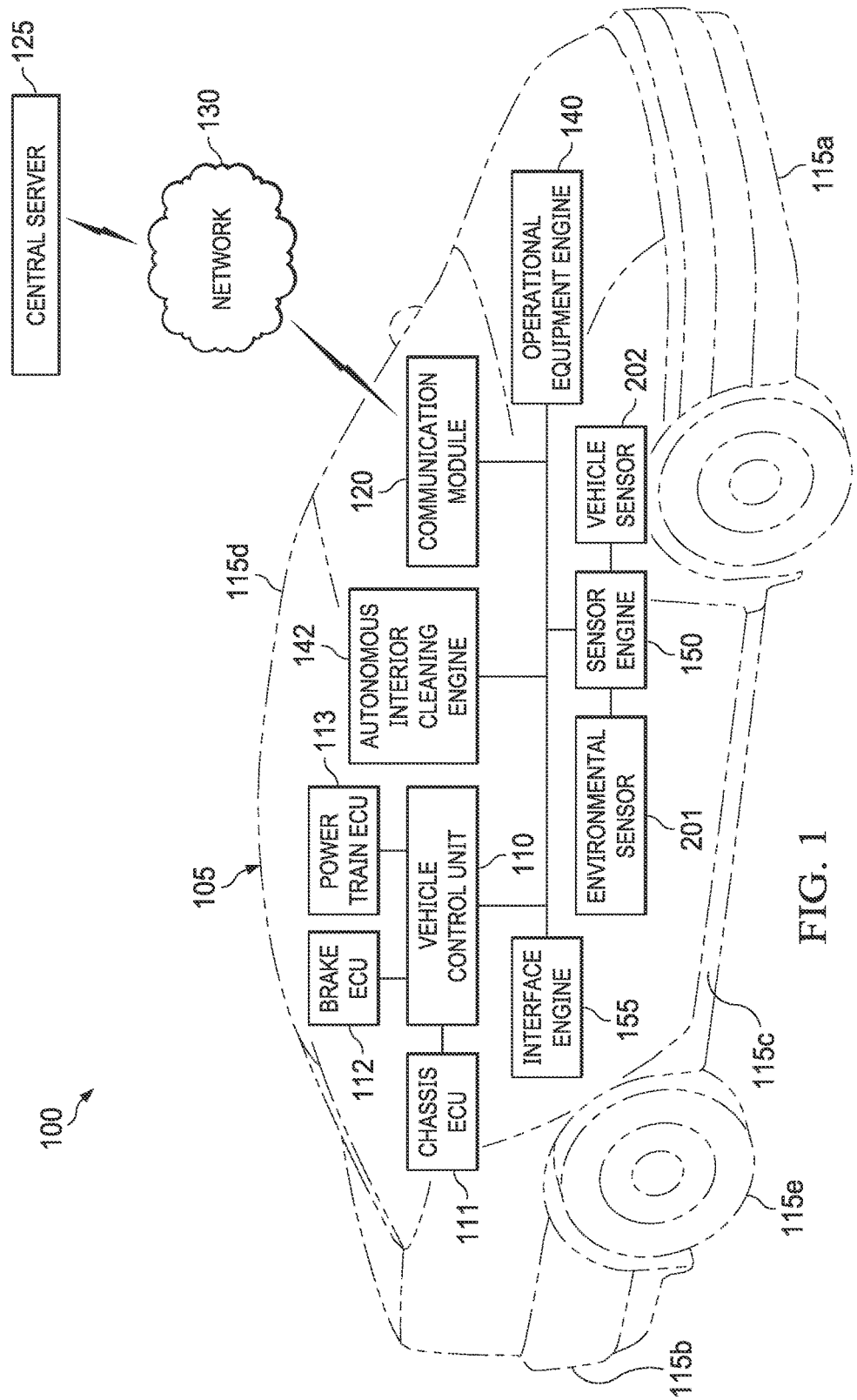
FIG. 1 is a diagrammatic illustration of an autonomous vehicle cleaning system, in accordance with at least one embodiment of the present disclosure.

Disclosed is an autonomous vehicle cleaning system that detects and addresses foreign material in a vehicle interior. This autonomous vehicle cleaning system may employ: UV, visible light, and infrared sensors, along with appropriate light sources, as well as 3D sensors, window dimming, autonomous driving, UV sterilization, or the dispensing of cleaning fluids. The autonomous vehicle cleaning system may for example be activated autonomously when all occupants have left the vehicle, and may detect the locations of stains, spills, dirt, trash, debris, and other foreign material, and may either attempt to clean them or may deliver the vehicle to a service location for cleaning. In some embodiments, the autonomous vehicle cleaning system controls dimmable windows and or moved the vehicle to a new location in order to adjust interior lighting conditions for optimal detection.

The present disclosure represents an improvement over the existing art, because it describes and enables a method that not only uses UV lights in an optimal manner (e.g., when no humans are present in the vehicle, vehicle located in areas with minimum sun exposure), but the vehicle also adjusts the vehicle seats so that the sanitizing lights can reach all areas that future passengers are likely to encounter. To ensure the minimum sun exposure, the vehicle may avoid sanitizing during the day or otherwise, travel to a dimly lit area (e.g., parking garage) or activate existing sun blocking systems (e.g., roller shades or curtains, sun visors, sunroof panels, and even controllable tinted windows).

Before every trip, or before every time a new passenger enters the vehicle, the vehicle's ground truth is established by taking two 3D recording of the vehicle's interior with the 3D LIDAR sensor and an alternate light source with corresponding imaging sensor. The first recording is of the vehicle interior with all of the seats in an upright position to capture most of the floor between the seats. The second recording is of the vehicle interior with all of the seats in full recline position to capture the entire seating surface, and (optionally) a stowed position where the entire cargo area may be captured by the imaging system for detecting debris and establishing a baseline ground truth that may be updated periodically.

The cleaning process then begins once the vehicle determines there are no humans or animals in the vehicle by using 3D LIDAR sensors, cameras, etc. Once it is determined that no living occupants are within the vehicle, the vehicle first dims all of the vehicle's windows to prevent sun exposure from affecting the cleaning process. In addition to or instead of dimming the windows, the vehicle may also drive to a shaded region or dark area to accomplish the same effect. Next, all foldable vehicle seats are stowed away to make room for the UV light to reach more spaces. Next, the UV light is turned on to sanitize the vehicle with the alternate light source turned off. The UV light is turned off either after a predetermined time or a calculated time for cleaning based on how dirty the car is. The alternate light source (e.g., a UV, violet, blue, or infrared light, such as a 1550 nm infrared light) is then turned on and a scene of the vehicle is recorded. By using the alternate light source, stains can be shown that a 3D LIDAR sensor or camera may not have picked up on. Next, a 3D profile of the vehicle cabin area is recorded using the 3D LIDAR sensor. Vehicle seats are then pulled back into an upright position to repeat the cleaning process, and the recording will be done for the vehicle cabin with seats in an unfolded position.

Both recordings are compared to the two established ground truths. If either of the recordings do not correspond to their respective ground truths, the vehicle will return to the step of cleaning with the UV light. In addition to UV lights, the vehicle could use aerosol sprays to clean the surfaces further.

Although the present disclosure provides a system to allow a self-driving or semi-autonomous vehicle to seek an ideal or optimal location (or provide instructions or a warning to a human driver to do so), the improved lighting condition need only improve the conditions, for example, by moving away from the interfering sunlight or street lamp to where it becomes sufficient to monitor the vehicle interior for spills and stains. Alternatively, where light is dim lit and lighting conditions are poor, the vehicle may also drive to a more optimal location or turn on exterior lights or open a closed garage to create a better lighting environment as well.

With the autonomous vehicle cleaning system of the present disclosure, a self-driving vehicle is able to drive to a new location or re-positioning the vehicle in a different orientation when light interferes with the stain detection means (e.g., camera or other imaging sensors) using the alternate light source (e.g., 1550 nm near-IR light). For example, where the light interferes with the imaging device's capabilities to detect stains, spills, dirt, or the like, the present invention provides a detection means for identifying when exterior lighting may interfere with the imaging device (or where lighting is poor or inadequate), whereupon the vehicle will move itself to seek optimal lighting conditions, for instance, by driving to a shaded area, into an indoor garage, or simply by turning the orientation of the vehicle to keep the exterior light from interfering with the receptors, lens, imaging capabilities or performance, and/or quality of the emitting rays that could compromise the system's ability to sense, receive or detect interior soils, stains and debris.

The present disclosure aids substantially in keeping vehicles (e.g., MaaS vehicles) clean, by improving detection and remediation of foreign material in between passenger pickups. Implemented as a system that integrates with existing vehicle components and subsystems, the autonomous vehicle cleaning system disclosed herein provides a practical means to detect foreign material and either clean it directly or else direct service personnel to clean it. This improved detection and cleaning process transforms potentially dirty vehicles into clean vehicles that are safer and more comfortable for passengers, without the normally routine need to wait until specified service times to clean the vehicle. This unconventional approach improves the functioning of the MaaS vehicle, by increasing in-service time and passenger comfort. A control process of the autonomous vehicle cleaning system may perform certain specific operations in response to different sensor inputs.

These descriptions are provided for exemplary purposes only, and should not be considered to limit the scope of the autonomous vehicle cleaning system. Certain features may be added, removed, or modified without departing from the spirit of the claimed subject matter. For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic illustration of an autonomous vehicle cleaning system, in accordance with at least one embodiment of the present disclosure. In an example, the autonomous vehicle cleaning system is referred to by the reference numeral 100 and includes a vehicle 105, such as an automobile, and a vehicle control unit 110 located on the vehicle 105. The vehicle 105 may include a front portion 115*a* (including a front bumper), a rear portion 115*b* (including a rear bumper), a right side portion 115*c* (including a right front quarter panel, a right front door, a right rear door, and a right rear quarter panel), a left side portion 115*d*

(including a left front quarter panel, a left front door, a left rear door, and a left rear quarter panel), and wheels 115*e*. A communication module 120 may be operably coupled to, and adapted to be in communication with, the vehicle control unit 110. The communication module 120 may in some cases be adapted to communicate wirelessly with a central server 125 via a network 130 (e.g., a 3G network, a 4G network, a 5G network, a Wi-Fi network, or the like). The central server 125 may provide information and services including but not limited to include location, mapping, route or path, and topography information.

An operational equipment engine 140 is operably coupled to, and adapted to be in communication with, the vehicle control unit 110. A sensor engine 150 is operably coupled to, and adapted to be in communication with, the vehicle control unit 110. The sensor engine 150 is adapted to monitor various components of, for example, the operational equipment engine 140. An interface engine 155 is operably coupled to, and adapted to be in communication with, the vehicle control unit 110. In addition to, or instead of, being operably coupled to, and adapted to be in communication with, the vehicle control unit 110, the communication module 120, the operational equipment engine 140, the sensor engine 150, and/or the interface engine 155 may be operably coupled to, and adapted to be in communication with, another of the components via wired or wireless communication (e.g., via an in-vehicle network). In some examples, the vehicle control unit 110 is adapted to communicate with the communication module 120, the operational equipment engine 140, the sensor engine 150, or the interface engine 155 to at least partially control the interaction of data with and between the various components of the system 100.

The term "engine" is meant herein to refer to an agent, instrument, or combination of either, or both, agents and instruments that may be associated to serve a purpose or accomplish a task—agents and instruments may include sensors, actuators, switches, relays, power plants, system wiring, computers, components of computers, programmable logic devices, microprocessors, software, software routines, software modules, communication equipment, networks, network services, and/or other elements and their equivalents that contribute to the purpose or task to be accomplished by the engine. Accordingly, some of the engines may be software modules or routines, while others of the engines may be hardware and/or equipment elements in communication with any or all of the vehicle control unit 110, the communication module 120, the network 130, or a central server 125.

In this example, the vehicle 105 also includes a chassis electronic control unit (ECU) 111 which controls elements of the vehicle's suspension system, a brake ECU 112 which controls the braking system or elements thereof, a power train ECU 113 (variously known as an engine ECU, power plant ECU, motor ECU, or transmission ECU) that controls elements of the motor and drivetrain. The system also includes one or more environmental sensors 201, one or more vehicle sensors 202, and an autonomous vehicle cleaning engine 142, the operation of which will be described below.

A reader of ordinary skill in the art will understand that other components or arrangements of components may be found in a vehicle 105, and that the same general principles apply to electric vehicles, internal combustion vehicles, and hybrid vehicles. For example, a power train ECU 113 may control both motor and transmission components. Alternatively, a separate motor ECU and transmission ECU may exist, or some functions of a motor ECU or transmission ECU may be performed by the VCU 110.

Before continuing, it should be noted that the examples described above are provided for purposes of illustration, and are not intended to be limiting. Other devices and/or device configurations may be utilized to carry out the operations described herein.

Figure 2:
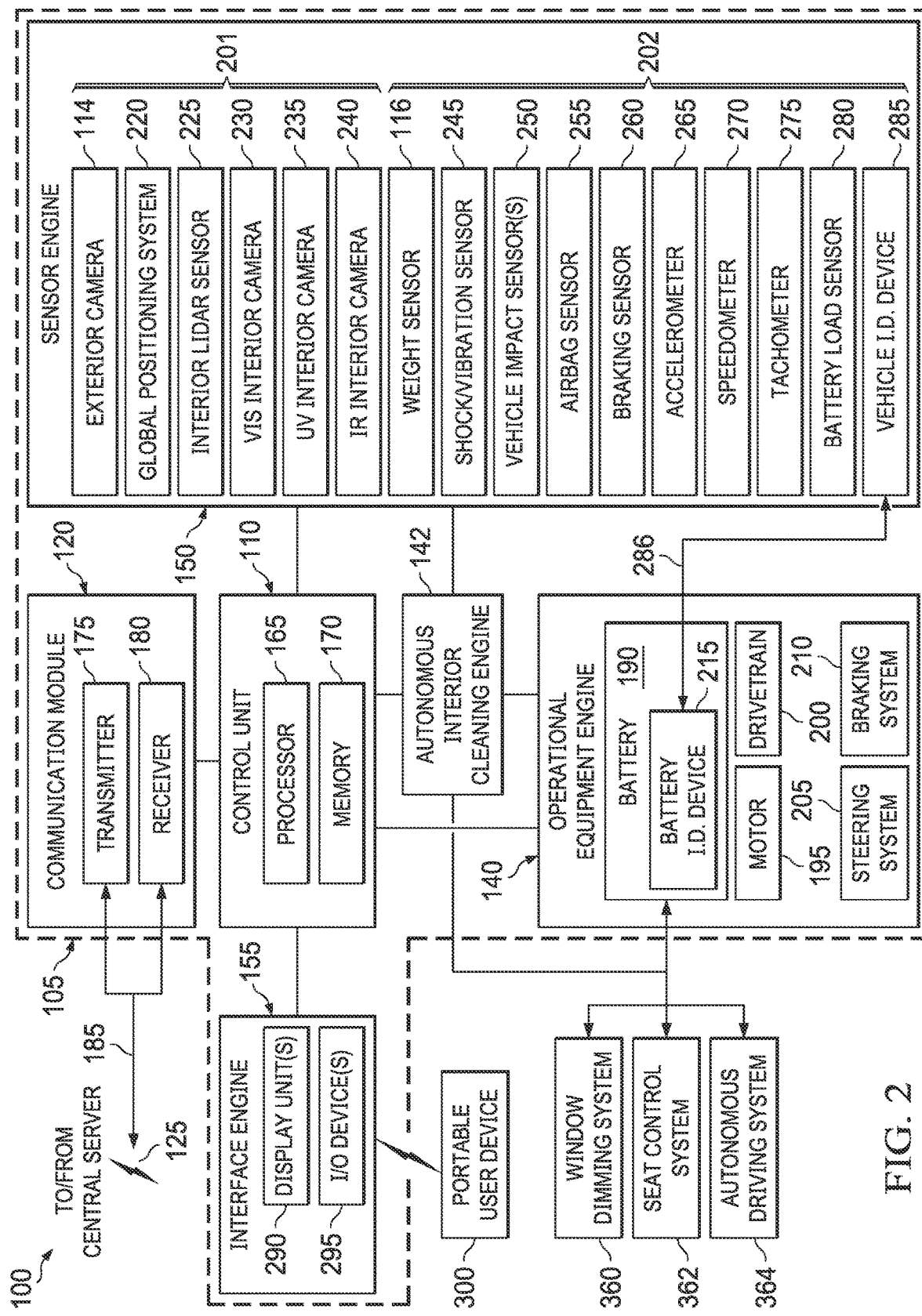
FIG. 2 is a diagrammatic illustration, in a block-diagram form, of at least a portion of the autonomous vehicle cleaning system of FIG. 1, in accordance with at least one embodiment of the present disclosure.

FIG. 2 is a diagrammatic illustration, in a block-diagram form, of at least a portion of the autonomous vehicle cleaning system 100 of FIG. 1, in accordance with at least one embodiment of the present disclosure. It is noted that the components of the vehicle 105 may be located either permanently or temporarily as a part of the vehicle 105. The vehicle control unit (VCU) 110 includes a processor 165 and a memory 170. In some examples, the communication module 120, which is operably coupled to, and adapted to be in communication with, the vehicle control unit 110, includes a transmitter 175 and a receiver 180. In some examples, one or the other of the transmitter 175 and the receiver 180 may be omitted according to the particular application for which the communication module 120 is to be used. In other examples, the transmitter 175 and receiver 180 are combined into a single transceiver that performs both transmitting and receiving functions.

In some examples, the operational equipment engine 140, which is operably coupled to, and adapted to be in communication with, the vehicle control unit 110, includes a plurality of devices configured to facilitate driving of the vehicle 105. In this regard, the operational equipment engine 140 may be designed to exchange communication with the vehicle control unit 110, so as to not only receive instructions, but to provide information on the operation of the operational equipment engine 140. For example, the operational equipment engine 140 may include a vehicle battery 190, a motor 195, a drivetrain 200, a steering system 205, and a braking system 210. In some vehicles, the vehicle battery 190 may provide electrical power to the motor 195 to drive the wheels 115*e* of the vehicle 105 via the drivetrain 200. In some examples, instead of or in addition to providing power to the motor 195 to drive the wheels 115*e* of the vehicle 105 via the drivetrain or transmission 200, the vehicle battery 190 provides electrical power to another component of the operational equipment engine 140, the vehicle control unit 110, the communication module 120, the sensor engine 150, the interface engine 155, or any combination thereof. In some examples, the vehicle battery 190 includes a battery identification device 215. In some embodiments, the motor is an internal combustion motor and the battery operates a starter.

In some examples, the sensor engine 150, which is operably coupled to, and adapted to be in communication with, the vehicle control unit 110, includes devices such as sensors, meters, detectors, or other devices configured to measure or sense a parameter related to a driving operation or other operation of the vehicle 105. For example, the sensor engine 150 may include a global positioning system 220, an interior lidar sensor 225, a visible light interior camera 230, an ultraviolet (UV) interior camera 235, an infrared interior camera 240, a shock/vibration sensor 245, a vehicle impact sensor 250, an airbag sensor 255, a braking sensor 260, an accelerometer 265, a speedometer 270, a tachometer 275, a battery load sensor 280, a vehicle identification device 285, an exterior camera 114, a weight sensor 116, or any combinations thereof. Any of the visible light interior camera 230, an ultraviolet (UV) interior camera 235, an infrared interior camera 240 may be employed as a light sensor for determining the amount of light that is present in the vehicle interior, or a separate light sensor may be provided. The sensors or other detection devices may be configured to sense or detect activity, conditions, and circumstances in an area to which the device has access, e.g., conditions inside or outside the vehicle cabin. Such sensors may include, but are not limited to, angle sensors, rotary encoders, or linear encoders. Sub-components of the sensor engine 150 may be deployed at any operational area where information on the status of the vehicle 105 may occur. Readings from the sensor engine 150 may be fed back to the vehicle control unit 110, or other control units. Stored and reported performance data may include the sensed data, or may be derived, calculated, or inferred from sensed data. The vehicle control unit 110 may send signals to the sensor engine 150 to adjust calibration or operating parameters of the sensor engine 150 in accordance with a control program in the vehicle control unit 110. The vehicle control unit 110 is adapted to receive and process performance data from the sensor engine 150 or from other suitable source(s), and to monitor, store (e.g., in the memory 170), and/or otherwise process (e.g., using the processor 165) the received performance data.

The braking sensor 260 is adapted to monitor usage of the vehicle 105's braking system 210 (e.g., an antilock braking system 210) and to communicate the braking information to the vehicle control unit 110. The accelerometer 265 is adapted to monitor acceleration of the vehicle 105 and to communicate the acceleration information to the vehicle control unit 110. The accelerometer 265 may be, for example, a two-axis accelerometer 265 or a three-axis accelerometer 265. In some examples, the accelerometer 265 is associated with an airbag of the vehicle 105 to trigger deployment of the airbag. The speedometer 270 is adapted to monitor speed of the vehicle 105 and to communicate the speed information to the vehicle control unit 110. In some examples, the speedometer 270 is associated with a display unit of the vehicle 105 such as, for example, a display unit of the interface engine 155, to provide a visual indication of vehicle speed to a driver of the vehicle 105. The tachometer 275 is adapted to monitor the working speed (e.g., in revolutions-per-minute) of the vehicle 105's motor 195 and to communicate the angular velocity information to the vehicle control unit 110. In some examples, the tachometer 275 is associated with a display unit of the vehicle 105 such as, for example, a display unit of the interface engine 155, to provide a visual indication of the motor 195's working speed to the driver of the vehicle 105. The battery load sensor 280 is adapted to monitor charging, discharging, and/or overcharging of the vehicle battery 190 and to communicate the charging, discharging, and/or overcharging information to the vehicle control unit 110.

In some examples, the vehicle identification device 285 stores data identifying the vehicle 105 such as, for example, manufacturing information (e.g., make, model, production date, production facility, etc.), vehicle characteristic(s) information, vehicle identification number ("VIN") information, battery compatibility information, or the like. The vehicle identification device 285 is adapted to communicate with the battery identification device 215 (or vice versa), as indicated by arrow 286. In some examples, the vehicle identification device 285 and the battery identification device 215 may each communicate with the vehicle control unit 110.

In some examples, the interface engine 155, which is operably coupled to, and adapted to be in communication with, the vehicle control unit 110, includes at least one input and output device or system that enables a user to interact with the vehicle control unit 110 and the functions that the vehicle control unit 110 provides. For example, the interface engine 155 may include a display unit 290 and an input/output ("I/O") device 295. The display unit 290 may be, include, or be part of multiple display units. In some examples, the display unit 290 may include one, or any combination, of a central display unit associated with a dash of the vehicle 105, an instrument cluster display unit associated with an instrument cluster of the vehicle 105, and/or a heads-up display unit associated with the dash and a windshield of the vehicle 105; accordingly, as used herein the reference numeral 290 may refer to one, or any combination, of the display units. The I/O device 295 may be, include, or be part of a communication port (e.g., a USB port), a Bluetooth communication interface, a touch-screen display unit, soft keys associated with a dash, a steering wheel, or another component of the vehicle 105, and/or similar components. Other examples of sub-components that may be part of the interface engine 155 include, but are not limited to, audible alarms, visual alerts, telecommunications equipment, and computer-related components, peripherals, and systems.

In some examples, a portable user device 300 belonging to an occupant of the vehicle 105 may be coupled to, and adapted to be in communication with, the interface engine 155. For example, the portable user device 300 may be coupled to, and adapted to be in communication with, the interface engine 155 via the I/O device 295 (e.g., the USB port and/or the Bluetooth communication interface). In an example, the portable user device 300 is a handheld or otherwise portable device (e.g., a smartphone or tablet computer) which is carried onto the vehicle 105 by a user who is a driver or a passenger on the vehicle 105, or proximate to the vehicle. In addition, or instead, the portable user device 300 may be removably connectable to the vehicle 105, such as by temporarily attaching the portable user device 300 to the dash, a center console, a seat back, or another surface in the vehicle 105. In another example, the portable user device 300 may be permanently installed in the vehicle 105. In some examples, the portable user device 300 is, includes, or is part of one or more computing devices such as personal computers, personal digital assistants, cellular devices, mobile telephones, wireless devices, handheld devices, laptops, audio devices, tablet computers, game consoles, cameras, and/or any other suitable devices. In several examples, the portable user device 300 is a smartphone such as, for example, an iPhone® by Apple Incorporated.

The autonomous vehicle cleaning system 100 also includes an autonomous vehicle cleaning engine 142, window dimming system 360, seat control system 362, and autonomous driving system 364, the operation of which will be described below. In some embodiments, the autonomous vehicle cleaning engine 142 comprises a standalone housing which may in some cases include a processor and memory. In other embodiments, the autonomous vehicle cleaning engine 142 may be operated by software, firmware, or hardware within another processor, such as the vehicle control unit 110, operational equipment engine 140, or power train ECU 113. The sensor engine 150 includes environmental sensors 201 and vehicle sensors 202. In an example, the autonomous vehicle cleaning engine 142 receives sensor data from one or more sensors.

A reader of ordinary skill in the art will understand that other components or arrangements of components may be found in a vehicle 105, and that the same general principles apply to electric vehicles, internal combustion vehicles, and hybrid vehicles.

Figure 3:
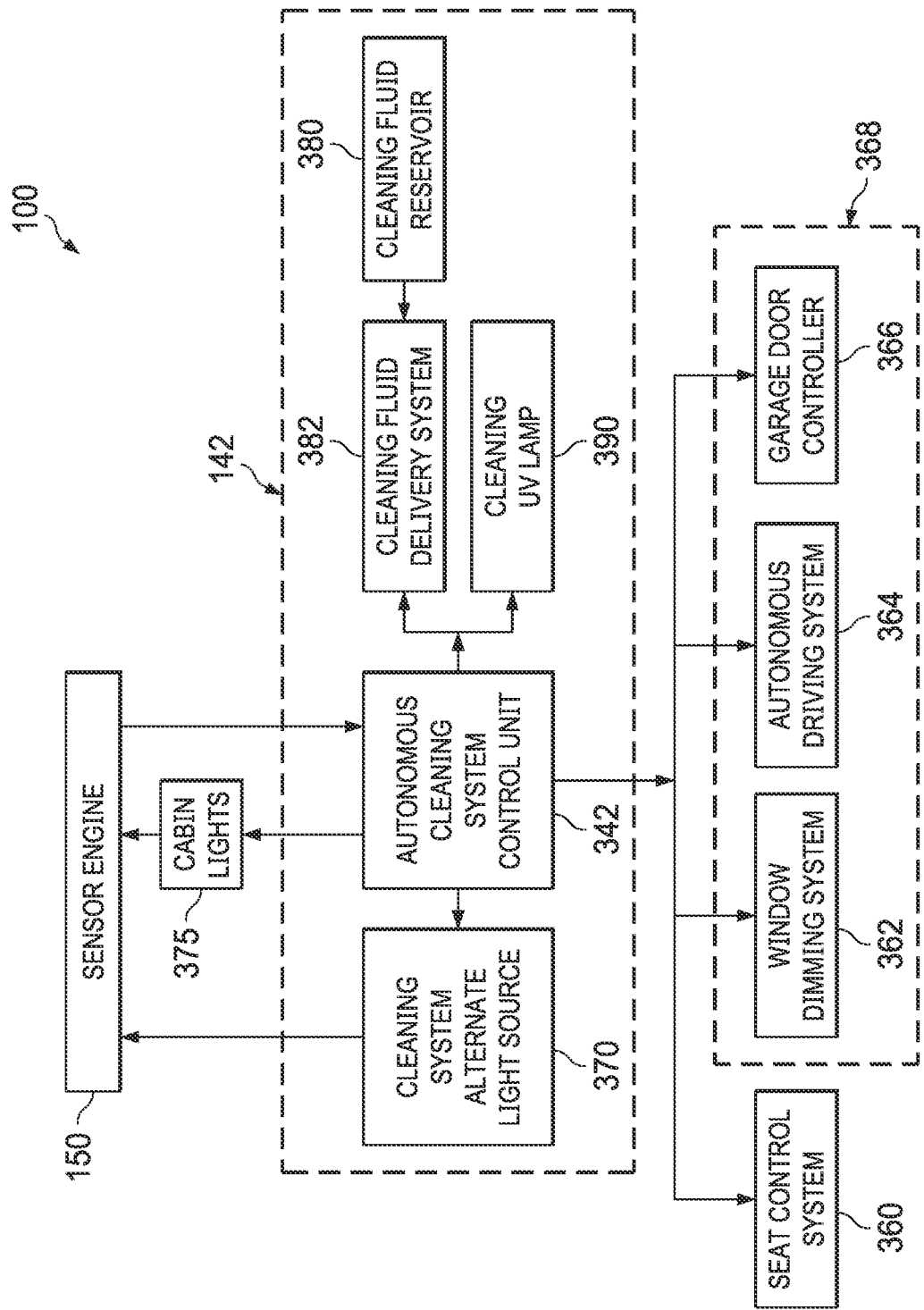
FIG. 3 is a schematic view, in block diagram form, of at least a portion of an example autonomous vehicle cleaning system, in accordance with at least one embodiment of the present disclosure.

FIG. 3 is a schematic view, in block diagram form, of at least a portion of an example autonomous vehicle cleaning system 100, in accordance with at least one embodiment of the present disclosure. In the example shown in FIG. 3, the autonomous vehicle cleaning system 100 includes an autonomous vehicle cleaning engine 142, which receives sensor information from the sensor engine 150. Such sensor information may include for example images from an interior lidar sensor 225, an interior visible light camera 230, an interior ultraviolet (UV) camera 235, or an interior near-infrared (NIR) camera 240. In some embodiments, two or more of the visible light camera 230, ultraviolet camera 235, or infrared camera 240 may be the same camera, operating with interchangeable filters or sensor elements.

The autonomous vehicle cleaning engine 142 may include various elements for inspecting and cleaning the interior of the vehicle. In the example shown in FIG. 3, the autonomous vehicle cleaning engine 142 includes an autonomous cleaning system control unit 342 (e.g., a processor with a memory), along with a cleaning system alternate light source 370, a cleaning fluid reservoir 380 and cleaning fluid delivery system 382, and a cleaning UV lamp 390, any of which may be activated by the autonomous cleaning system control unit 342 at different times, as described below. The autonomous cleaning system control unit 342 may also activate: a seat control system 360 to control the position and recline of vehicle seats; a window dimming system 362 to darken the vehicle windows and thus darken the interior of the vehicle; and an autonomous driving system 364 to instruct the vehicle to darken the interior of the vehicle by driving to a darkened area such as a tunnel or parking garage. Alternatively, the autonomous cleaning system control unit 342 may instruct a human driver (e.g., via the interface engine 155, portable user device 300, or communication module 120) to drive to a desired location, possibly with the aid of a global positioning system 220. In some embodiments, the window dimming system controls the dimming of the windows through automatic shades, louvres, curtains, visors, or electrochromic elements coated onto or embedded within the windows, or other devices that have the effect of reducing the amount of light from external sources (e.g., sunlight) that is able to enter the vehicle interior.

The autonomous cleaning system control unit 342 may detect trash or other foreign objects using the lidar sensor 225, by capturing a 3D point cloud of the vehicle interior and comparing it to a stored baseline or nominal point cloud of an empty vehicle. The autonomous cleaning system control unit 342 may also detect stains and spills using a visible light interior camera 230, ultraviolet interior camera 235, or infrared interior camera 240.

A visible light camera 230 may image the vehicle interior using visible light emitted by the cabin lights 375, which may be switched on or off by the autonomous cleaning system control unit 342. In some embodiments, the visible light camera may include one or more swappable or non-swappable filters to restrict certain wavelengths of light. An ultraviolet interior camera 235 or infrared interior camera 240 may image the interior using ultraviolet light or infrared light emitted by the cleaning system alternate light source 370, which may for example be a blue lamp emitting at a wavelength of 450-490 nanometers (nm), a violet lamp emitting at a wavelength of 400-450 nm, a near-UV (NUV) lamp emitting at a wavelength of 260-400 nm, or a near-infrared (NIR) lamp emitting at a wavelength of 800-1600 nm. In an example a NIR lamp may emit at, and a NIR camera may image at, a wavelength of 800 nm, 1310 or 1550 nm, which have shown utility for imaging stains and for showing contrast between differing materials that may, to the human eye under visible light, appear to be the same color.

An alternate light source 370 comprising a blue, violet, or UV lamp may cause certain stains or spills to fluoresce, such that they can be imaged by a visible light camera 230, with or without a filter, even if the stains would be difficult to resolve with a visible light camera under ambient (e.g., white) light. A UV cleaning lamp 390 may for example emit UV-A radiation at a wavelength of 315-400 nm, UV-B radiation at a wavelength of 280-315 nm, or UV-C radiation at a wavelength of 100-280 nm. UV-C radiation may be more effective than UV-A or UV-B at killing or inactivating microorganisms, breaking down organic molecules, and bleaching out stains, but may also accelerate aging of materials (e.g., polymers) comprising the automotive interior. Ultraviolet light may be harmful to humans, and may therefore be activated by the autonomous cleaning system control unit 342 only when the control unit 342 has confirmed that no humans are present within the vehicle, and that all doors and windows are closed. In some embodiments, an alternate light source UV lamp 370 and a cleaning UV lamp 390 may be the same lamp. Not all of the elements shown will necessarily be present in a given embodiment. Other elements or components may be present instead of or in addition to those shown, and the arrangement or relationships between the elements may differ, without departing from the spirit of the present disclosure. Some elements may be combined. For example, in some embodiments, the autonomous cleaning system control unit 342 may be incorporated into the vehicle control unit 110.

In some instances, a window dimming system 362 and autonomous driving system 364 may both be components of an external light control system 368, whose purpose is to control the amount of external light (e.g., sunlight) entering the vehicle interior. In some embodiments, the external light control system may include other features, such as a garage door controller 366 capable of opening or closing a garage door, or commanding a garage door to open or close, in order to adjust the amount of external light entering the vehicle interior.

Figure 4:
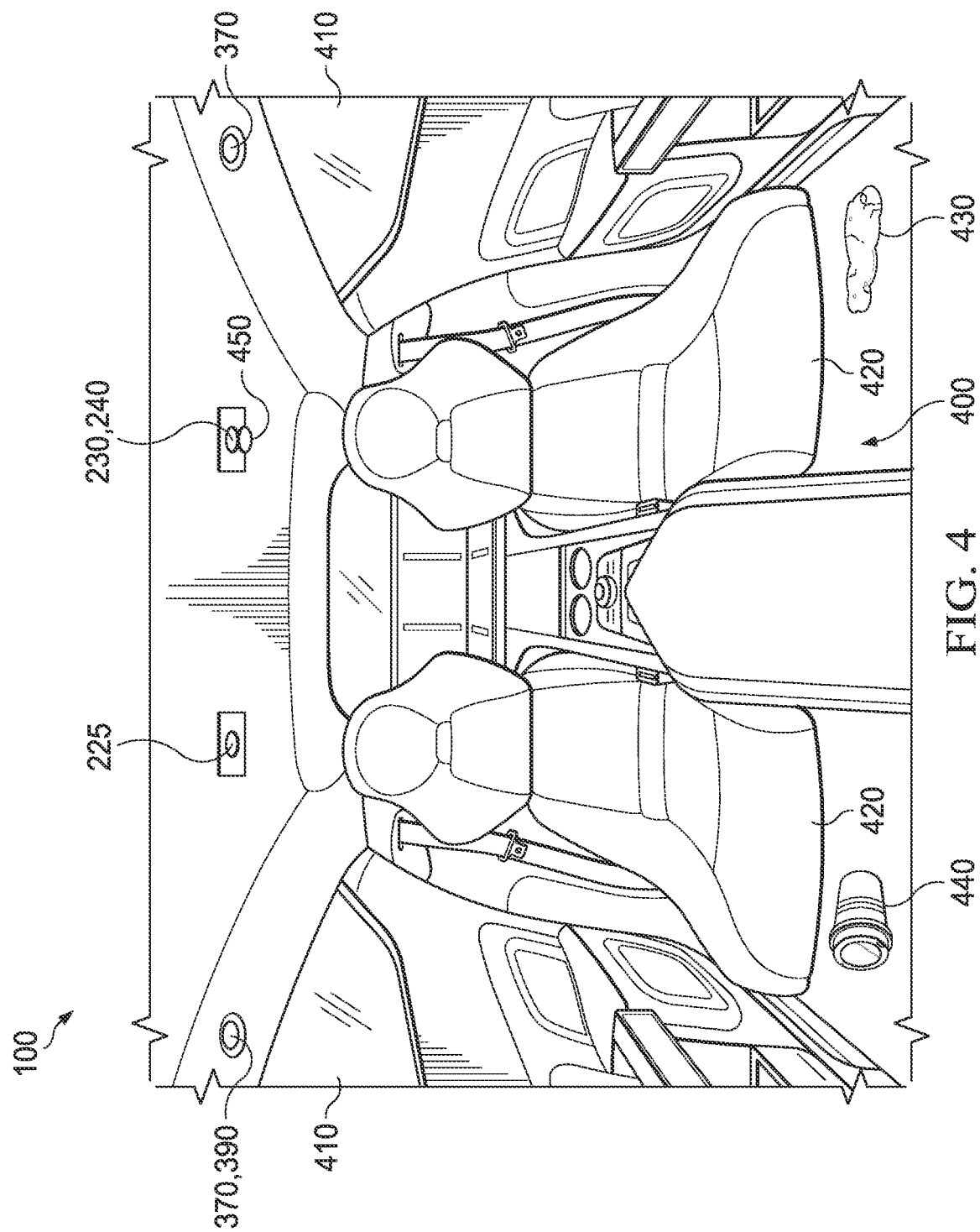
FIG. 4 is a perspective view of a vehicle interior incorporating at least a portion of an example autonomous vehicle cleaning system, in accordance with at least one embodiment of the present disclosure.

FIG. 4 is a perspective view of a vehicle interior 400 incorporating at least a portion of an example autonomous vehicle cleaning system 100, in accordance with at least one embodiment of the present disclosure. In the example shown in FIG. 4, the vehicle interior 400 includes dimmable windows 410, a combined UV alternate light source 370 and UV cleaning lamp 390, an interior lidar 225, a combined visible light interior camera 230 and infrared interior camera 240 with an automatically swappable filter 450, and an infrared alternate light source 370.

The vehicle interior 400 also includes movable seats 420, which can be controlled via the seat control system 360 under the command of the autonomous cleaning system control unit 342. For example, the seats 420 may be moved forward, moved backward, folded, unfolded, reclined, un-reclined, raised, or lowered in order to access to different parts of the vehicle interior 400. For example, moving the seats may permit the lidar 225 and the camera 230, 240 to image different portions of the vehicle interior 400, and also permit the cleaning UV lamp 390, or a cleaning fluid delivery system 382, to clean different portions of the vehicle interior 400. In an example, a surface of the vehicle interior 400 includes a stain 430 which is visible to the camera 230, 240 only when the seats 420 are moved all the way backward. Other possible stains 430 might be visible to the camera 230, 240 when the seats are forward, folded, unfolded, raised, reclined, or otherwise. In this example, a surface of the vehicle interior 400 also includes a foreign object 440 (e.g., a cup, wrapper, receipt, etc.) that is visible to the camera 230, 240, and/or the lidar 225, only when the seats 420 are in certain positions.

Figure 5:
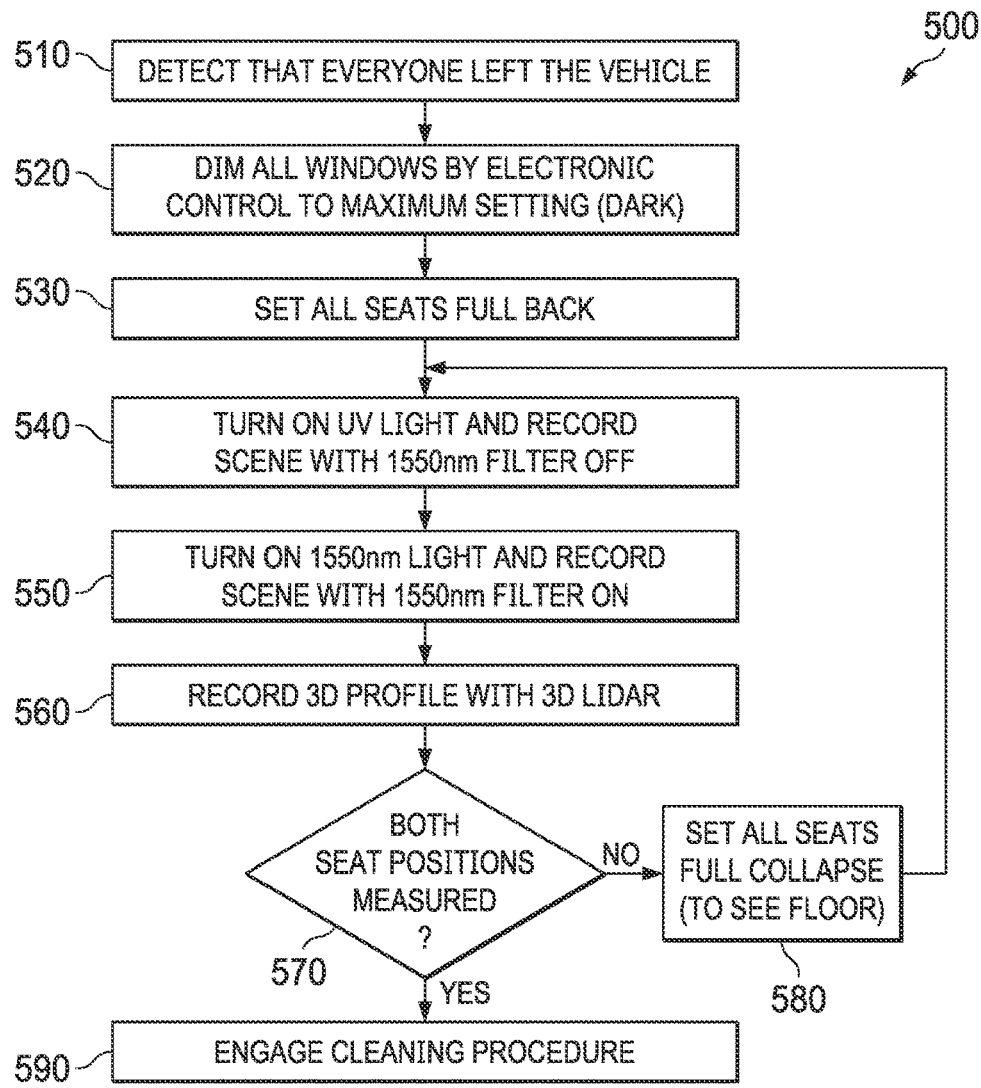
FIG. 5 is a flow diagram showing an example autonomous vehicle cleaning method 500, in accordance with at least one embodiment of the present disclosure.

FIG. 5 is a flow diagram showing an example autonomous vehicle cleaning method 500, in accordance with at least one embodiment of the present disclosure. It should be understood that the steps of method 500 may be performed in a different order than shown in FIG. 5, additional steps can be provided before, during, and after the steps, and/or some of the steps described can be replaced or eliminated in other embodiments. One or more of steps of the method 500 can be carried by one or more devices and/or systems described herein, such as elements of the sensor engine 150, vehicle control unit 110, autonomous interior cleaning engine 142, autonomous cleaning system control unit 342, window dimming system 360, seat control system 362, autonomous driving system 364, or other elements or processors present in the vehicle, as appropriate.

In step 510, the method 500 includes detecting whether the vehicle is empty of human or animal occupants. Such detection may involve interior lidar sensor 225 or cameras 230, 235, or 240, along with an image recognition, shape recognition, or movement recognition algorithm running on the VCU 110, autonomous cleaning system control unit 342, or other processor. If human or animal occupants are detected within the vehicle, step 510 may continue until the vehicle is detected to be empty, at which point execution proceeds to step 520.

In step 520, the amount of light entering the vehicle interior is restricted. In some embodiments, this may be accomplished for example by measuring the amount of light inside or outside the vehicle using an exterior camera 114 or interior visible light camera 230, and then dimming the dimmable windows 410 (whether electrochromically or by other means). In other embodiments this dimming may be accomplished by instructing an autonomous driving system 364 to drive the vehicle to a darkened area such as a tunnel or parking garage. In still other embodiments, dimming may be accomplished by waiting until after sunset. Once the vehicle interior is suitably dim, or isolated from exterior light, execution proceeds to step 530.

In step 530, vehicle seats 420 are moved to desired positions (e.g., all the way forward or all the way back) to expose, for inspection and cleaning, certain surfaces or portions of surface of the vehicle interior 400. This may be accomplished for example through commands sent from the autonomous cleaning system control unit 342 to the seat control system 360. Execution then proceeds to step 540.

In step 540, the scene is imaged with a camera and light source, in order to look for stains, spills, dirt, mud, or other foreign material. This may for example involve activating a blue, violet, or UV alternate light source 370 and imaging the vehicle interior 400 with a visible light camera 230, with or without a filter (e.g., an orange or yellow bandpass filter to exclude the blue, violet, or UV light of the alternate light source). Such an arrangement may cause certain materials to fluoresce such that they emit visible light and are more easily distinguished from the vehicle materials on which they have been deposited. In this sense, the visible light emitted by foreign materials may be considered to have been generated by the alternate light source. Images captured by the camera can then be compared against a stored baseline image of a clean vehicle, such that differences between the current image and the baseline image can be flagged as stains or spills. Execution then proceeds to step 550.

In step 550, the scene is imaged with a different combination of camera and light source, in order to look for stains, spills, dirt, mud, or other foreign material. This may for example involve activating an infrared light source 370 and imaging the vehicle interior 400 with an infrared camera 240, with or without a filter (e.g., an infrared bandpass filter to exclude all wavelengths except that of the IR lamp 370). Such an arrangement may cause certain dirt, stain, or spill materials to stand out (e.g., as light or dark spots) against the materials of the vehicle interior, even if, under white light with a visible light camera, they would appear invisible. Images captured in this way can then be compared against a stored baseline image of a clean vehicle, such that differences between the current image and the baseline image can be flagged as stains or spills. Execution then proceeds to step 560.

In step 560, the vehicle interior is imaged (e.g., as a point cloud) using a 3D sensing device such as a lidar 225, although other sensing devices may be used instead or in addition, including a 3D camera, radar, or sonar. The resulting 3D image can then be compared against a stored baseline 3D image, and any differences between the current image and the baseline image can be flagged as trash. Execution then proceeds to step 570.

In step 570, the method determines whether the vehicle interior has been imaged in all desired seat positions. If the answer is no, execution proceeds to step 580. If the answer is yes, execution proceeds to step 590.

In step 580, the vehicle seats 420 are moved to a new desired position (e.g., all the way forward, all the way folded, etc.), and execution then returns to step 540.

In step 590, the vehicle interior has been imaged in all desired seat positions, and the locations of dirt, dust, stains, spills, trash, debris, and other foreign material have been identified. The method then engages a cleaning procedure. In some embodiments, the cleaning procedure may involve activation for a set period of time of a cleaning element. The cleaning element may for example be a UV cleaning lamp 390 or a cleaning fluid delivery system 382 such as a spray nozzle that draws fluid (e.g., solvents, antiseptics, degreasers, deodorizers, or perfumes) from a cleaning fluid reservoir 380. In other embodiments, the cleaning procedure may involve notifying a service crew (e.g., via the communications module 120) of the presence and locations of foreign material and then instructing the autonomous driving system 364 to drive the vehicle to a service location. In still other embodiments, the cleaning procedure may involve notifying a vehicle owner or operator (e.g., via the communications module 120, or via a display under the control of the interface engine 155 or portable user device 300) of the presence and locations of foreign material, and permitting the vehicle owner or operator to take appropriate action.

In some embodiments, method 500 is activated once, after all vehicle occupants have departed the vehicle. In other embodiments, the method 500 may be activated multiple times, to assess the success of previous cleaning attempts. In some embodiments, depending on the locations of foreign material in the vehicle interior, the cleaning procedure may be activated multiple times while the seats are in different positions, e.g., after step 560 and before step 570.

Figure 6:
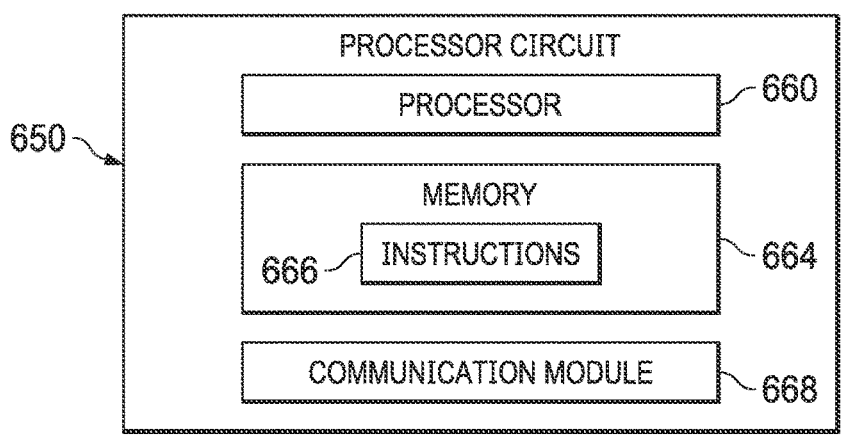
FIG. 6 is a diagrammatic illustration of a processor circuit, according to embodiments of the present disclosure.

FIG. 6 is a diagrammatic illustration of a processor circuit 650, according to embodiments of the present disclosure. The processor circuit 650 may be implemented in the autonomous vehicle cleaning system 100, VCU 110, portable device 300, or other devices or workstations (e.g., third-party workstations, network routers, etc.), or on a cloud processor or other remote processing unit, as necessary to implement the method. As shown, the processor circuit 650 may include a processor 660, a memory 664, and a communication module 668. These elements may be in direct or indirect communication with each other, for example via one or more buses.

The processor 660 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 660 may also comprise another hardware device, a firmware device, or any combination thereof configured to perform the operations described herein. The processor 660 may also be implemented as a combination of computing devices, e.g., a combination of a DSP and a microprocessor, a plurality of microprocessors, one or more microprocessors in conjunction with a DSP core, or any other such configuration.

The memory 664 may include a cache memory (e.g., a cache memory of the processor 860), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 664 includes a non-transitory computer-readable medium. The memory 664 may store instructions 666. The instructions 666 may include instructions that, when executed by the processor 660, cause the processor 660 to perform the operations described herein. Instructions 666 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 668 can include any electronic circuitry and/or logic circuitry to facilitate direct or indirect communication of data between the processor circuit 650, and other processors or devices. In that regard, the communication module 668 can be an input/output (I/O) device. In some instances, the communication module 668 facilitates direct or indirect communication between various elements of the processor circuit 650 and/or the autonomous vehicle interior cleaning engine 142. The communication module 668 may communicate within the processor circuit 650 through numerous methods or protocols. Serial communication protocols may include but are not limited to US SPI, I²C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and a central server, or readings from the sensors) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

As will be readily appreciated by those having ordinary skill in the art after becoming familiar with the teachings herein, the autonomous vehicle cleaning system advantageously permits a MaaS vehicle to clean itself in between passenger pickups, even in hard-to-reach areas, and/or to identify messes that require human intervention to clean, and to deliver the vehicle to a service location with detailed instructions as to the locations of the foreign material. A number of variations are possible on the examples and embodiments described above. For example, other elements, or other combinations of elements, may be present in the automotive interior 400 or autonomous interior cleaning engine 142 to achieve the desired result of autonomous cleaning of the vehicle interior. Such elements may include for example other sensors, other light sources, other cleaning agents, and other means of controlling interior lighting. Elements can vary in size, shape, position, mechanism of operation, and mode of operation without departing from the spirit of the present disclosure. Multiple cleaning mechanisms can be provided. The technology described herein may be applied to myriad different vehicle types, including internal combustion, electric, and hybrid vehicles, cars, trucks, vans, campers, and other vehicles, including off-road vehicles, aircraft, watercraft, or spacecraft, whether manually operated, driver-tended, fully autonomous, or MaaS.

The logical operations making up the embodiments of the technology described herein are referred to variously as operations, steps, objects, elements, components, or modules. It should be understood that these may be performed in any order, unless explicitly claimed otherwise or a specific order is inherently necessitated by the claim language. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the autonomous vehicle cleaning system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." The word "comprising" does not exclude other elements or steps, and the indefinite article "a" or "an" does not exclude a plurality. Unless otherwise noted in the claims, stated values shall be interpreted as illustrative only and shall not be taken to be limiting.

The above specification, examples and data provide a complete description of the structure and use of exemplary embodiments of the autonomous vehicle cleaning system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter.

Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. A vehicle comprising:
   an interior and an exterior;
   a surface disposed within the interior;
   a movable seat positioned over a first portion of the surface;
   a processor;
   a seat control system configured to, under control of the processor, move the movable seat such that the first portion of the surface is exposed;
   a light source configured to, when activated by the processor after the seat control system has moved the movable seat, illuminate a second portion of the surface, wherein the second portion includes the first portion;
   a sensor configured to, under control of the processor, capture an image of the second portion of the surface while the second portion of the surface is illuminated by the light source; and
   a cleaning element configured to, when activated by the processor, clean the second portion of the surface,
      wherein the processor is configured to detect foreign material on the second portion of the surface based on a comparison between the image and a stored image,
      wherein the processor is configured to, after detecting the foreign material on the second portion of the surface, activate the cleaning element.

2. The vehicle of claim 1, wherein the light source and the sensor comprise a lidar.

3. The vehicle of claim 1, wherein the light source comprises an ultraviolet (UV) light source, and the sensor comprises a UV, visible light, or infrared (IR) sensor.

4. The vehicle of claim 1, wherein the light source comprises a visible light source, and the sensor comprises a visible light camera.

5. The vehicle of claim 1, wherein the light source comprises an infrared light source, and the sensor comprises an infrared sensor.

6. The vehicle of claim 1, wherein the cleaning element is a UV lamp or a cleaning fluid delivery system.

7. The vehicle of claim 1, further comprising windows configured to dim or brighten under the control of the processor, wherein the processor is configured to activate the light source while the windows are dimmed.

8. The vehicle of claim 7, wherein the dimming or brightening comprises automatic curtains, shades, louvres, visors, or electrochromic elements.

9. The vehicle of claim 1, wherein the processor is configured to, after detecting the foreign material on the surface, issue an alert through a display or communication module.

10. The vehicle of claim 1, further comprising an autonomous driving system configured to, under control of the processor, drive the vehicle to a destination.

11. The vehicle of claim 10, wherein the destination comprises dim lighting, and wherein the processor is configured to activate the light source while the vehicle is in the destination.

12. The vehicle of claim 10, wherein the destination is a service location, and wherein the processor is configured to, after detecting the foreign material, control the autonomous driving system to drive the vehicle to the destination.

13. A method for cleaning an interior surface of a vehicle, the method comprising:
   providing a movable seat positioned over a first portion of the interior surface;
   under control of a processor, moving the movable seat to expose the first portion;
   under control of the processor after the movable seat has been moved, activating a light source to illuminate a second portion of the interior surface, wherein the second portion includes the first portion;
   with a sensor under control of the processor, capturing an image of the second portion while the second portion is illuminated by the light source;
   with the processor, based on a comparison between the image and a stored image, detecting foreign material on the second portion; and
   with the processor, after detecting the foreign material, activating a cleaning element to clean the second portion.

14. The method of claim 13, wherein:
   the light source is a laser, UV light source, visible light source, or infrared light source, and wherein the sensor is configured to detect light produced by the light source; or
   the cleaning element is a UV lamp or cleaning fluid delivery system.

15. The method of claim 13, further comprising dimming the vehicle interior before activating the light source.

16. A system for cleaning a surface in an interior of a vehicle, the system comprising:
   the vehicle, wherein the vehicle comprises an interior and an exterior;
   a surface disposed within the interior;
   a movable seat positioned over a first portion of the surface;
   a processor;
   a light sensor configured to detect a lighting condition of the interior;
   an external light control system configured to, under control of the processor and based on the detected lighting condition of the interior, adjust an amount of external light entering the vehicle to a desired amount; and
   an autonomous cleaning system disposed within the interior and configured to be activated by the processor after the amount of external light entering the vehicle has been adjusted to the desired amount.

17. The system of claim 16, wherein adjusting the amount of external light entering the vehicle comprises:
   adjustably dimming one or more windows of the vehicle, and wherein the vehicle comprises automatic curtains, shades, louvres, visors, or electrochromic elements configured to adjustably dim the one or more windows;
   driving the vehicle to a location with a desired amount of external light, and wherein the external light control system comprises an autonomous driving system configured to drive the vehicle to the location; or at least partially opening or closing a garage door, and wherein the external light control system comprises an automatic garage door controller.

18. The system of claim 16, further comprising:
a seat control system configured to, under control of the processor, move the movable seat such that the first portion of the surface is exposed;
a light source comprising a laser light source, UV light source, visible light source, or infrared light source, wherein the light source is configured to, when activated by the processor after the seat control system has moved the movable seat, illuminate a second portion of the surface, wherein the second portion includes the first portion; and
a sensor configured to:
  detect light produced by the light source; and
  under control of the processor, capture an image of the second portion of the surface while the second portion of the surface is illuminated by the light source,
wherein the processor is configured to detect foreign material on the second portion of the surface based on a comparison between the image and a stored image.

19. The system of claim 18, wherein the autonomous cleaning system comprises:
a cleaning element configured to, when activated by the processor, clean the second portion of the surface,
  wherein the cleaning element is a UV lamp or a cleaning fluid delivery system,
  wherein the processor is configured to, after detecting the foreign material on the second portion of the surface, activate the cleaning element.

20. The system of claim 19, further comprising an alert, issuable via a display or communication module under control of the processor, indicating that the foreign material has been detected on the second portion of the surface.

* * * * *